(12) United States Patent
Schiavon et al.

(10) Patent No.: US 6,790,942 B1
(45) Date of Patent: Sep. 14, 2004

(54) BIOLOGICALLY ACTIVE CONJUGATES HAVING A DETECTABLE REPORTER MOIETY AND METHOD OF IDENTIFICATION OF THE DERIVATIVE

(75) Inventors: Oddone Schiavon, Padua (IT); Francesco Veronese, Padua (IT); Paolo Caliceti, Padua (IT); Piero Orsolini, Martigny (CH)

(73) Assignee: Debio Recherche Pharmaceutique, Martigny (CH)

( * ) Notice: Subject to any disclaimer, the term of this patent is extended or adjusted under 35 U.S.C. 154(b) by 0 days.

(21) Appl. No.: 09/857,469

(22) PCT Filed: Dec. 8, 1999

(86) PCT No.: PCT/IB99/01957

§ 371 (c)(1),
(2), (4) Date: Jun. 5, 2001

(30) Foreign Application Priority Data

Aug. 12, 1998 (EP) .............................................. 98123307

(51) Int. Cl.$^7$ .......................... C12N 11/06; C07K 19/00; A61B 5/055; A61K 39/00; C07H 21/04
(52) U.S. Cl. ........................ 530/402; 530/402; 435/181; 424/9.35; 424/198.1; 536/24.2
(58) Field of Search ................................ 435/181, 180; 260/112.5, 112.7; 424/78, 94, 177, 178, 198.1, 9.35; 530/402; 536/24.2

(56) References Cited

U.S. PATENT DOCUMENTS 5,286,637 A   2/1994  Veronese et al.

FOREIGN PATENT DOCUMENTS

| EP | 0 536 671 | 4/1993 |
|---|---|---|
| WO | WO 91/01758 | 2/1991 |
| WO | WO 92/20362 | 11/1992 |

OTHER PUBLICATIONS

Sartore, et al, 1991, Appl. Biochem. Biotechnol., 27(1): 55–63.*
Lapicque et al, "Polysaccharidic Prodrugs for Enzymatically Controlled Release", Journal of Controlled Release, 4, 1986, pp. 39–45.
De Marre et al, "Evaluation of the hydrolytic and enzymatic stability of macromolecular Mitomycin C derivatives", Journal of Controlled Release, 31, 1994, pp. 89–97.
Harris, Introduction to Biotechnical and Biomedical Applications of Poly(Ethylene Glycol), Poly(Ethylene Glycol) Chemistry: Biotechnical and Biomedical Applications, ed.: J.M. Harris et al, 1992, pp. 1–14.
Veronese et al, "New Synthetic Polymers for Enzyme and Liposome Modification", Poly(Ethylene Glycol) Chemistry: Chemistry and Biological Applications, ed.: J.J. Harris et al., ACS Symposium Series 680, 1997, pp. 182–192.

Abuchowski et al, "Alteration of Immunological Properties of Bovine Serum Albumin by Covalent Attachment of Polyethylene Glycol", The Journal of Biological Chemistry, 252, 1977, pp. 3578–3581.
Abuchowski et al., Effect of Covalent Attachment of Polyethylene Glycol on Immunogenicity and Circulating Life of Bovine Liver Catalase, The Journal of Biological Chemistry, 252, 1977, pp. 3582–3586.
Beauchamp et al, "A New Procedure for the Synthesis of Polyethylene Glycol–Protein Adducts; Effects on Function, Receptor Recognition and Clearance of Superoxide Dismutase, Lactoferrin, and $\alpha_2$–Macroglobulin", Analytical Biochemistry, 131, 1983, pp. 25–33.
Veronese et al, "Surface Modification of Proteins, Activation of Monomethoxy–Polyethylene Glycols by Phenylchloroformates and Modification of Ribonuclease and Superoxide Dismutase", Applied Biochemistry and Biotechnology, 11, 1985, pp. 141–152.
Zalipsky et al, "Attachment of Drugs to Polyethylene Glycols", European Polymer Journal, 19, 1983, pp. 1177–1183.
Delgado et al., "The Uses and Properties of PEG–Linked Proteins", Critical Reviews in Therapeutic Drug Carrier Systems, 9, 1992, pp. 249–304.
Morpurgo et al, "Preparation and Characterization of Poly(ethylene glycol) Vinyl Sulfone", Bioconjugate Chemistry, 7, 1996, pp. 363–368.
Clark et al, "Long–acting Growth Hormones Produced by Conjugation with Polyethylene Glycol", The Journal of Biological Chemistry, 271, 1996, pp. 21969–21977.
Vestling et al, "A Strategy for Characterization of Polyethylene Glycol–Derivatized Proteins", Drug Metabolism and Disposition, 21, 1993, pp. 911–917.
Sartore et al, Enzyme Modification by MPEG with an Amino Acid or Peptide as Spacer Arms, Applied Biochemistry and Biotechnology, 27, 1991, pp. 45–54.
Gross, "The Cyanogen Bromide Reaction", Methods in Enzymology, 1967, pp. 238–255.
Winter, "Manual Sequencing by the Dansyl–Edman Reaction", Practical Protein Chemistry, ed. A. Darbre, 1986, pp. 367–374.

* cited by examiner

Primary Examiner—Elizabeth Kemmerer
Assistant Examiner—Sandra Wegert
(74) Attorney, Agent, or Firm—Nixon & Vanderhye P.C.

(57) ABSTRACT

Biologically active drug polymer derivatives, namely peptides or protein derivatives, are useful medicaments and are represented by the generic formula: RO—(CH$_2$—CH$_2$O)$_n$—(CO)—NH—X—(CO)—NH—Z wherein R represents a lower alkyl group, n is an integer between 25 and 250, X when combined with adjcacent NH and CO groups represents a dipeptide residue, and Z when combined with the adjacent group represents a biologically active peptide or protein.

15 Claims, 6 Drawing Sheets a)

b)

BIOLOGICALLY ACTIVE CONJUGATES HAVING A DETECTABLE REPORTER MOIETY AND METHOD OF IDENTIFICATION OF THE DERIVATIVE

The present invention concerns a conjugate derivative, in particular a polymer conjugate derivative, of a biological active molecule such as a protein, a peptide, a polypeptide. The present invention concerns also a method of chemical identification of said conjugate derivative.

Although a great number of new peptides and proteins with potentially useful pharmacological activities are now synthesised thanks to genetic engineering, their therapeutic potential is often drastically limited by negative properties that are intrinsic to their chemical structure. For example, polypeptides, once administered, may often be easily cleaved by endo- or exo-proteases, be rapidly excreted by renal filtration, and may often provoke immunological reactions, in spite of possessing human sequences. Furthermore, the size and nature of the macromolecule can dictate a targeting inside the body that is not always the one desired for their therapeutic action.

Conjugation at the protein surface of biocompatible, non toxic, non immunogenic, water soluble polymers, has been found to be a procedure that may reduce these problems and allows for, in few cases, useful therapeutic applications. A polymer often used for such conjugation is poly(ethyleneglycol) (PEG) due in part to its very favourable biological properties, (see "Poly(ethylene glycol) chemistry and biological application" M. J. Harris Ed. Plenum Press, (1994), (incorporated herein by reference) as well as dextran, albumin, poly(N-vinylpyrrolidone), and poly(N-acryloylmorpholine, among others. "New synthetic polymers for enzyme and liposome modification Poly(ethylene glycol), p.182, ACS Symp Series 680, 1997, also discloses some of the later polymers.

Proteins and peptides have also being conjugated to antibodies and other high affinity ligands in order to target to a specific site inside the body.

Various amino acid residues in proteins, have been found suitable for polymer conjugation, including, for example, the amino groups of lysine and the alpha amino terminal groups. The thiol group of cysteine, guanidino group of arginine and the terminal carboxylic group, as well as the carboxylic group of aspartic or glutamic acids have been considered. Reported studies and methodologies for modification of protein amino groups include those of Davies and Abuchowski (Abuchowski et al. 1977a and 1977b), those of Benchamp et al., 1983, Veronese et al., 1985, Zalipsky et al., 1983, Delgrado et al., 1990. Protein SH group modification is described in the work of Morpurgo et al., 1996, while guanidino modification is described by Pande et al. Polysaccarides residues, when present in proteins, have been exploited more rarely, and principally, for binding. However, among these residues the conjugation to the amino groups is by far the most important one.

In spite of the current state of knowledge related to polymer conjugation in prodrugs preparations, it remains true that since in polypeptides and proteins all of these groups are present in a number that may be very high, (and also the groups themselves present different exposure at the macromolecule surface, or possess different nucleophylicity), an heterogeneous and complex pattern of products is generally obtained. Up to the present time it has remained very difficult to state the position of polymer conjugation in the primary sequence of the protein with much success.

This difficulty is compounded by the fact that it is extremely difficult, if not impossible, in the majority of the cases, to fractionate the different conjugates from the conjugation mixture, even when the most sophisticated methods now available are employed. The hindrance of the protein molecule may mask the charges at the protein surface, thus reducing the binding to ion exchange resins, as well as the selectivity of binding to affinity ligands, and reduces the potentials of various methods, including gel filtration chromatography, in accomplishing this task.

Various approaches have been reported in the literature on the identification of the conjugation site, especially when an high molecular polymer is the conjugation species.

One approach is based on the comparison of the finger printings, obtained by HPLC, in the case of the PEG-conjugated product with that obtained in the case of the native unconjugated polypeptide. Though some information on binding sites was obtained on the basis of the identification of the missing PEG peptides in the tryptic digest of the conjugate, this information relied on the assumption that trypsin does not act where PEG is bound or in its close surroundings, and that there is no resultant release of the corresponding peptides.

Though this approach was found useful in the study of the peptide growth hormone (Ross Clark et al. J. Biol. Chem. 271, 21969–21977, 1996), it cannot be always considered conclusive because it is based on indirect evidence, and relies on a method that can give information on the site of binding of PEG only in the cases of relatively short polypeptides that give rise to simple patterns of proteolitic digestion.

Another approach was based on the protein "PEGilation" with a polymer that carries a succinic acid arm between PEG and protein. Succinic acid was linked to PEG by a labile ester function and to protein by a stable amide. The PEG chains were removed from the protein by mild basic hydrolysis of the labile ester bond that links PEG to succinic acid, while leaving succinic acid moiety, as a reporter group, linked to the residues where PEG was bound, with labelled peptides then recognised by mass spectrometry (M. M. Vestling et al. Drug Metab. Disp. 21, 911–917). There are at least two severe limitations of this method: the first resides in the linking chemistry of PEG to protein, whereby the chemistry is not generally considered appropriate or convenient for products of human use, because the ester linkage between PEG and succinic acid may be easily cleaved in physiologic circulation, giving rise to new products; the second limitation resides in the fact that the identification of the succinic acid labelled peptide, in the peptide map, may be carried out by mass spectrometry only. Standard amino acid analysis, which is the usual method for sequence studies, cannot be applied in such a case since, during the strong acid hydrolysis that has to be done before the amino acid identification (AAA), the succinic acid moiety is removed from the amino acid where it is bound. For this reason one cannot identify by the most accurate AAA procedure the peptides where succinic acid was bound. Furthermore, the weakness of the same bond hampers the use of other important procedures of sequence analysis determinations.

U.S. Pat. No. 5,286,637 (Veronese et al.), issued Feb. 15, 1994, also describes an approach and a method using M-PEG. The method of their invention is based on the linkage of art amino acid or peptide spacer arm of various structures and properties to the hydroxyl function of monoalkoxypolyethylene glycol through a carbonate linkage which involves the $NH_2$ group of the amino acid or peptide. This reaction is followed by the activation of the COOH function of the amino acid or peptide spacer arm as succinimidyl ester which, thus, becomes reactive towards the amino group of the biologically active peptide, protein or drug. Use of this method has the disadvantage, common to all methods of conjugation of PEG chains, to hamper the use of most, if not all, of the fractionation procedures of the conjugate product, as well as a suitable fractionation of the PEGylated digestion mixture.

For this reason, the exact identification of the site of polymer binding into the protein remains a still problem, when preparing the corresponding prodrug, although it is an essential prerequisite for a rational drawing of correlation between structure and activity of the prodrug conjugates. The knowledge of this correlation may be in fact one of the most useful guides to design new conjugates with more convenient pharmacokinetic, pharmacological and therapeutic properties.

The exact identification of the site of conjugation is also important for a more precise analytical characterisation of a biological active macromolecular product, particularly when the conjugate is intended for therapeutic use, and requires an accurate characterisation in order to meet health authority requirements.

The importance of finding a method for identifying the original location of the functional entity is demonstrated in the use of macromolecules in therapy: there, conjugates are necessary. In such conjugates, (which can use in therapeutical applications, for example, a PEG+protein combination), the PEG may be linked to many different sites on the macromolecule. It is important to have a method to discover at exactly which site or sites the PEG+protein linked to the macromolecule was bound. The present invention retains an attached amino acid reporter moiety, thereby helping identify and describe, through analysis, the conjugation product.

The aims of the present invention are to provide with biological active conjugate derivatives while overcoming the limitations reported in the aforementioned procedures for the polymer modifications of polypeptides and proteins.

To that effect, one of the objects of the present invention is a biological active conjugate derivative having the following general formula (I)

where:
M represents the corresponding radical of a biological active molecule selected from the group consisting of proteins, peptides and polypeptides;
FE represents a functionalizing entity; and
L represents a linking arm having a reporter moiety detectable by standard analytical methods, the linking arm being able to be cleaved by chemical or enzymatic in vitro treatment, the reporter moiety remaining attached to the biological active molecule once the linking arm has been cleaved.

According to the present invention, it has been found that specific spacer groups lead to the possibility to remove the functional entity FE from the conjugate with a diminished harshness to avoid destroying or otherwise denaturing the molecule, while retaining an attached amino acid reporter moiety to the molecule for identification.

The linking arm L is stable under physiological conditions but cleavable by specific and selective physical-chemical means, whereby a stable reporter moiety detectable by standard analytical methods remains attached to M and thereby its presence may optionally be identified by mass spectroscopy and may be cleaved by chemical or enzymatic treatment for evaluation by standard amino acid analysis.

An alternative identification procedure may include Maldi mass spectroscopy analysis of an uncleaved conjugate.

Preferably, in the biological active conjugate derivative according to the present invention, the functionalizing entity FE is selected from PEG, PVP, PacM, dextran, hormones, antibodies or antibody fragments. More preferably, the functionalizing entity FE is a polymer with a molecular weight in the range of 2 Kd to 50 Kd. The functionalizing entity FE can be either a linear polymer or a branched polymer.

Preferably, in the biological active conjugate derivative according to the present invention, the linking arm L comprises the following fragment Met-X in which X represents the reporter moiety and the reporter moiety is an amino acid. More preferably, the amino acid X is selected from Nle and beta Ala.

Also preferably, the linking arm L comprises either the dipeptide Gln-Gly or Asp-Pro.

Preferably, in the biological active conjugate derivative according to the present invention, the radical M corresponds to a biological active molecule and said molecule is a protein selected from insulin, lysozime, interferon, in particular interferon α-2b, erithropoietin, G-CSF, GH.

Another object of the present invention is a method for identifying, is on the above mentioned biological active drug conjugate derivative, sites of conjugation of the functionalizing entity FE along the biological active molecule M comprising a specific chemical or enzymatic in-vitro cleavage of the linking arm L, releasing, removing and separating FE by classical methods.

Another object of the present invention is an intermediate compound, for the preparation of the biological active conjugate of claim 1, having the following general formula (II)

where:
FE represents a functionalizing entity; and
L represents a lining arm having a reporter moiety detectable by standard analytical methods.

The reporter moiety is useful to identify the original location of the functional entity. The present inventions described in detail below, takes advantage of the use of a special PEG amino acid sequences, in which PEG may be released in such a way to leave a reporter amino acid bound to the macromolecule that is exploited for the identification of the site of PEG binding.

Without limitation and in the spirit of the invention, several functionalizing entities can be foreseen—for example, FE is typically a polymer when M is intended for therapeutic applications. While many polymers may be included in the present invention, preferentially, the polymer may be selected from the group consisting of PEG, PVP, PAcM, dextran and others. Even more preferred in PEG, PVP and PacM. Even more preferred is PEG for its very favourable biological properties. Even more preferred is MPEG.

As described above, FE, as described in the present invention, may be a polymer or functional entity consisting of polymers. Preferably, the FE/Polymer has a molecular weight greater than 2 kd; more preferably, the molecular weight is in the range of 2 to 50 kd. When FE is a polymer, FE can be a linear or branched polymer.

Other functionalizing entities can be included in the present invention, for example high affinity ligands for targeting to specific sites. FE, in this case, may be any of a number of high affinity ligands. Preferably, FE can be an hormone, antibody, or an antibody fragment, or a compound selected with high output technique to a recognition site. More preferably, FE can be selected from the group consisting of antibody(ies) or antibody fragment(s).

The linking arm L may be preferably devised to react with amino groups from the M moiety such as the alpha amino or the epsilon amino group of lysine. Preferably the linking arm L may be represented by an activated carboxilic group of amino acid. Most preferably, an unnatural amino acid, nor-leucine or beta-alanine is preferred for its easier identification after acid hydrolysis.

When the derivative compound has the following structure:

FE-Met-X-M,

X is a suitable reporter group such as an either unnatural or natural amino acid. Preferably the unnatural amino acid is nor-leucine (Nleu) or the amino acid beta-alanine(beta-Ala), which is absent among the protein constituents. Also of preference are other amino acids which are non common constituents of proteins.

X may be bound to the protein M by, for example, stable amide linkage, through procedures known to the man of ordinary skill in the art. The advantage to use of these types of amino acids as reporters resides in the fact that, not being natural constituents of the proteins, they are very convenient in analysis—their presence indicates and quantifies the previous presence of PEG.

In the case of one or more of these more preferred embodiments of the present invention, FE can be removed from the protein by selective CNBr treatment, leaving X still covalently bound to M by a stable amide bond.

When the conjugate has the following structure:

FE-Gln-Gly-M, specific removal of FE can be preferentially obtained by hydrazine treatment, leaving the amino acid Gly bound to M.

When the conjugate has the following structure:

FE-Asp-Pro-M, specific removal of FE can be obtained by mild acid treatment, leaving Pro still bound to M.

In the above specified embodiments of the present invention, the M bound reporter moieties are very stable to acid hydrolysis and therefore easily identified by the standard amino acid analysis following acid hydrolysis, as well as by mass spectrometry if the non hydrolysed peptide containing them is analysed by this technique. Preferably, M bound reporter moieties are selected from the group of Nle, betaAla, Gly or Pro. More preferably, M bound reporter moieties are selected from unnatural amino acids, Nle or beta Ala. Even more preferably, the reporter moiety is norleucine.

It is particularly preferred in the present invention, and particularly using Met-X, that one uses Nle or betaAla as amino acid reporter moieties.

In general, in a main embodiment of the present invention, the method of the present invention consists of identifying or analysing linkage sites on macromolecules using a compound having the composition FE-L-M by identifying the binding site of FE on to the M moiety based on a specific physical—chemical cleavage of L and, thereafter, releasing, removing and separating FE by chromatographic methods.

The suitability of the general methods of the present invention is demonstrated further by the using as non-limiting examples (the localisation of the site of PEG conjugation in the primary sequence of a PEGilated non-apeptide and insulin, either when insulin was PEGilated at one or at the level of two amino groups).

In a specific embodiment of the present invention the polypeptides were modified by PEG-Met-Nle. The conjugation of PEG to the therapeutically relevant protein, lysozime, followed by its complete removal by CNBr, is thereby illustrated.

In several embodiments of the present invention, several PEG peptide derivatives compounds are illustrated as examples of the structure: FE-L.

Among these, the following are reported as illustrative and appear in several examples: PEG-Met-Nle, PEG-Met-Val, PEG-Met-β-Ala, PEG-Gln-Gly, PEG-Asp-Pro. All of these selected PEG derivative compounds of the present invention were activated at the terminal COOH with one of the methods reported in the literature, namely hydroxysuccinimidylester (OSu), and were then coupled to the representative polypeptides and proteins.

As additional preferred embodiment of the present invention, lysozime was PEGilated with PEG-Met-Nle, activated as OSU, and in turn, the polymer moiety was removed by CNBr treatment.

In all of these above selected example embodiments the FE-L-M complexes, after conjugation, were purified by HPLC or FPLC treatment in order to remove the activated unreacted polymer as well as the unmodified M.

As a further step, the purified conjugates were examined and the composition quantified, in a preferred way, by amino acid analysis after acid hydrolysis in order to evaluate, on the basis of the ratio of the reporter amino acid group to the amino acid content of M, (as well as by mass spectrometry of the non hydrolysed derivative), the number of polymer chains that were bound to M.

Furthermore, by trinitrobenzenesulphonate (TNBS) calorimetric assay, the purified conjugates were analysed to evaluate the number of the amino groups that did not react, (and by iodine assay, specific for PEG) in a preferred embodiment, to reveal its presence.

For the compounds and using the method of the present invention, analyses demonstrate that all of the FE-L were linked to the polypeptides similarly to what occurs when PEG is activated according to other procedures. It was also found that the increase in molecular weight, as evaluated by the Maldi mass spectrometry, corresponds to the polypeptide molecular weight increased of the FE-L weight or of its multiples. Furthermore, the presence of the reporter amino acid groups in the polypeptide could surprisingly always be revealed and quantitatively evaluated by amino acid analysis, and the value obtained corresponded to the modification calculated on the basis of the amino groups calorimetric evaluation. Finally it was found that in all of the cases the conjugates are reactive to iodine and a decrease or disappearance of polypeptide amino groups takes place at an extent that corresponds to the number of bound FE-L.

In the method of the present invention, after removal of PEG by the aforementioned procedure, the PEG-free polypeptide is purified by gel filtration from where it is eluted at higher volume due to its reduction in weight. The new elution volume approximately corresponds to that of M before the PEG modification; in theory, the small difference being due to the increase in weightowing to the binding of the reporter group that remains bound to M after FE removal.

Steps of sequence structure evaluation, such as Edman degradation, reduction and carboxymethylation, or proteolitic degradation could also be used in the present invention to indicate the site of PEG attachment, with easier detection of the reporter amino acid by amino acid analysis after acid hydrolysis or, when possible, mass spectrometry of the non-hydrolysed peptide.

Some of these interesting properties are illustrated in the following Examples, which are not limitative, and with the following analitical spectra where:

EXAMPLE 1

Synthesis of MPEG-Met-Val-OH (5000 Da)

MPEG-OH 5000 (where MPEG is Poly(ethylene glycol) methyl ether), dissolved in anhydrous methylene chloride, was reacted with 4-nitrophenyl chloroformate at pH 8 in the presence of equimolecular amount of triethylammine to give MPEG-p-nitrophenylcarbonate 1 g of the product (0.19 mmol) was added in small portions to 283 mg (1.14 mmol) of H-Met-Val-OH dissolved in 4 ml of a 50% acetonitrile solution in water and brought to pH 8 with TEA. After overnight stirring, the pH of the reaction mixture was adjusted to 3 using solid citric acid; 4-nitrophenol was removed by ether extraction while the product was later extracted by chloroform. The organic solution was anhydrified with solid dry Na$_2$SO$_4$ and concentrated under reduced pressure. After the addition of 200 ml of diethyl ether to the chloroform, the solution was cooled at −20° C. for 1 hour and the separated product was collected by filtration and dried under vacuum. The MPEG-Met-Val-OH was further purified by ionic exchange chromatography on a QAE-Sephadex® A50 column (2.5×55 cm), eluted first with water and then with a water solution of NaCl 10 mM. The. eluted fractions were analysed by iodine assay to detect PEG. The fractions containing the sodium salt of MPEG-peptide were collected, acidificated and lyophilised. The yield was 70–75% in MPEG-peptide. The product was identified by $^1$H-NMR (200 MHz; CDCl$_3$).

EXAMPLE 2

Synthesis of MPEG-Met-Nle-OH (5000 Da)

MPEG 5000 was bound to Met-OH to obtain MPEG-Met-OH following the method described in example 1 in the preparation of MPEG-Met-Val-OH. 523 mg (2.88 mmol) of H-Nle-OMe and a equimolecular amount of TEA (401 µl) were added to absolution of 10 ml of anhydrous dichloromethane, containing 3.71 g (0.72 mmol) of the synthesised MPEG-Met-OH, 305 mg (0.72 mmol) of 1-cyclohexyl-3-(2-morpholinoethyl)carbodiimidemetho-p-toluenesulfonate (CMC) and 97 mg (0.72 mmol) of 1-hydroxybenzotriazole (HOBt). After stirring for 3 days at room temperature, the mixture was dropped into 250 ml of diethyl ether; the precipitate was collected by filtration and dried under vacuum. The product was further purified by ionic exchange chromatography on a QAE-Sephadex® A50 column (2.5×55 cm) eluted first with water and then with a water solution of NaCl 10 mM. The fractions were analysed by iodine assay to reveal the presence of PEG. The fractions containing the MPEG-peptide-methyl ester (MPEG-Met-Nle-OMe), were collected and lyophilised. The yield was 93%. The structure of the product was verified by $^1$H-NMR (200 MHz; CDCl$_3$).

Figure 1:
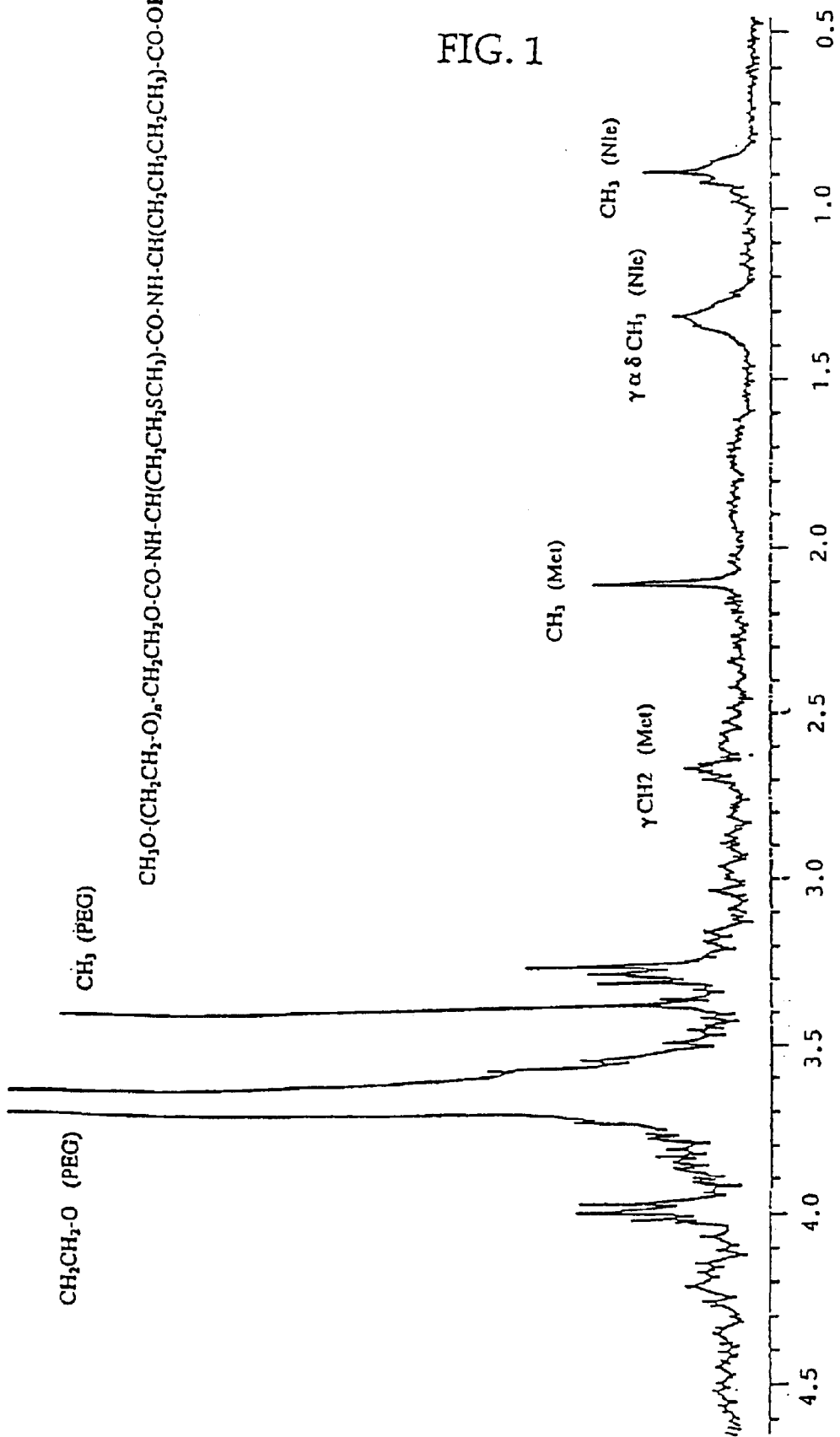
FIG. 1 is the $^1$H-NMR spectrum of MPEG-Met-Nle-OH in CDCl$_3$.

The methyl ester of Nle was hydrolysed in a solution of methanol containing 20 equivalents of NaOH 1N, left stirring the mixture for 2 days at room temperature. The solution pH was brought to 2 using HCl 1N and the product extracted into chloroform. The chloroform solution was anhydrified with solid dry Na$_2$SO$_4$ and concentrated under reduced pressure. The addition of 200 ml of diethyl ether, under vigorous stirring, yielded a solid product that was collected by filtration and dried under vacuum. The yield was 67% in MPEG-Met-Nle-OH. The product identity was verified by $^1$H-NMR (200 MHz, CDCl$_3$). The spectrum is reported in FIG. 1.

EXAMPLE 3

Synthesis of MPEG-Met-Nle-OH (10000 Da)

The product was prepared according to example 2 but starting from a MPEG-OH of 10000 MW.

EXAMPLE 4

Synthesis of (MPEG-Met-Nle)$_2$-nonapeptide

The MPEG-Met-Nle-OH terminal COOH was activated as hydroxysuccinimidil ester (MPEG-Met-Nle-OSu) according to a method already reported in literature for MPEG with Nle as aminoacid spacer (*Applied Biochemistry and Biotechnology*, 27, 45–54, 1991).

Totally protected nonapeptide obtained by solid phase synthesis with the following structure Nps-Thr(tBu)-Ser(tBu)-Asp(OtBu)-Tyr(tBu)-Ser(tBu)-Lys-(Boc)-Tyr(tBu)-Leu-Asp(OtBu)-OH was deprotected maintaining it in a 1:1 mixture of trifluoroacetic acid and dichloromethane, for 2 hours at room temperature. The solution was concentrated to dryness and the Nps group removed by repeated extractions in diethyl ether at 0° C. The product was finally dried under vacuum for 12 hours over KOH. The yield of the totally deprotected peptide was 90%.

43 mg (4.0 mmol) of MPEG-Met-Nle-OSu were added, in small portions, to 0.9 mg (0.8 µmol) of the deprotected nonapeptide dissolved in 1 ml of DMSO, at pH 8 with TEA. (nonapeptide:MPEG-Met-Nle-OSu molar ratio=1:5). After 3 days stirring at room temperature, the pH of the reaction mixture was adjusted to 3 using HCl 1N and the product was extracted many times into chloroform. The chloroform solution was anhydrified with solid dry Na$_2$SO$_4$ and concentrated to dryness. The conjugate was further purified by means of a Shimadzu semi-preparative HPLC system, using a reverse-phase Vydac® 218TP54 column (C$_{18}$ bonded-phase, 0.46×25 cm i.d, 5 µm particle diameter) and a linear gradient of aqueous 0.05% trifluoroacetic acid and 0.05% trifluoroacetic acid in acetonitrie. The absorption at 280 nm wavelength was monitored. The product was characterised by iodine assay for MPEG and aminoacid analysis.

EXAMPLE 5

Synthesis of MPEG-Met-Nle-insulin 8.6 mg (1 µmol) of MPEG-Met-Nle-OSu prepared as in example 4, were added to 6 mg (1 µmol) of bovine insulin dissolved in 1 ml of DMSO (amino groups of insulin:MPEG molar ratio=3:1) and the mixture was left stirring for 5 hours at room temperature. The conjugate was purified by means of a Shimadzu preparative HPLC system, using a reverse-phase Vydac® 218TP1022 column ($C_{18}$ bonded-phase, 2.2× 25 cm i.d., 10 um particle diameter) and a linear gradient of aqueous 0.05% trifluoroacetic acid and 0.05% trifluoroacetic acid in acetonitrile, monitoring the absorption at 280 nm wavelength. The fractions of the main elution peak of conjugated insulin were collected and lyophilised. The identity of the product was evaluated by amino groups colorimetric assay that indicated the loss of one amino residue in insulin and by aminoacid analysis after acid hydrolysis that revealed one Nle per insulin, again in favour of binding of a single polymer chain per insulin molecule.

EXAMPLE 6

Synthesis of (MPEG-Met-Nle)$_2$-insulin 17 mg (2 µmol) of MPEG-Met-Nle-OSu prepared as in example 4, were added to 6 mg (1 µmol) of bovine insulin dissolved in 1 ml of DMSO ml (amino groups of insulin-:MPEG molar ratio=3:2). After stirring for 5 hours at room temperature, the product was purified by reverse-phase HPLC as described in example 5 for MPEG-Met-Nle-insulin. The fractions of the main elution peak of conjugated insulin were collected and lyophilised. The identity of the conjugate was evaluated by amino groups colorimetric assay that indicated the loss of two amino residues and by aminoacid analysis after acid hydrolysis that demonstrated the presence of two Nle per insulin, indicating the binding of two PEG moiety per insulin molecule.

EXAMPLE 7

Reaction of (MPEG-Met-Nle)$_2$-nonapeptide with CNBr 1 mg (85.2 µmol) of (MPEG-Met-Nle)$_2$-nonapeptide, obtained as described in example 4 was treated with 100 equivalents of CNBr in aqueous 70% formic acid (according to *Methods in Enzymology*, pag. 238–254, 1967). After 24 hours standing at room temperature, the mixture was poured into 10 volumes of water and lyophilised. (the procedure was repeated twice). The obtained products were analysed by means of a Shimadzu analytical HPLC system, using a reverse-phase Vydac® 218TP54 column ($C_{18}$ bonded-phase, 0.46×25 cm i.d., 5 um particle diameter) and a linear gradient of aqueous 0.05% trifluoroacetic acid and 0.05% trifluoroacetic acid in acetonitrile. The elution pattern indicated a shift in the elution times from the 36.3 min. for the PEG-peptide conjugate, to 15.8 min. for the same product upon treatment with CNBr. This value was close to that of the peptide alone (16.4 min.) demonstrating that the PEG moiety was removed. Aminoacid analysis after acid hydrolysis and mass spectrometry revealed the presence of two Nle residues per peptide molecule, indicating the validity of this method in removing PEG from the molecule leaving Me as reported group bound to the polypeptide.

EXAMPLE 8

Figure 2:
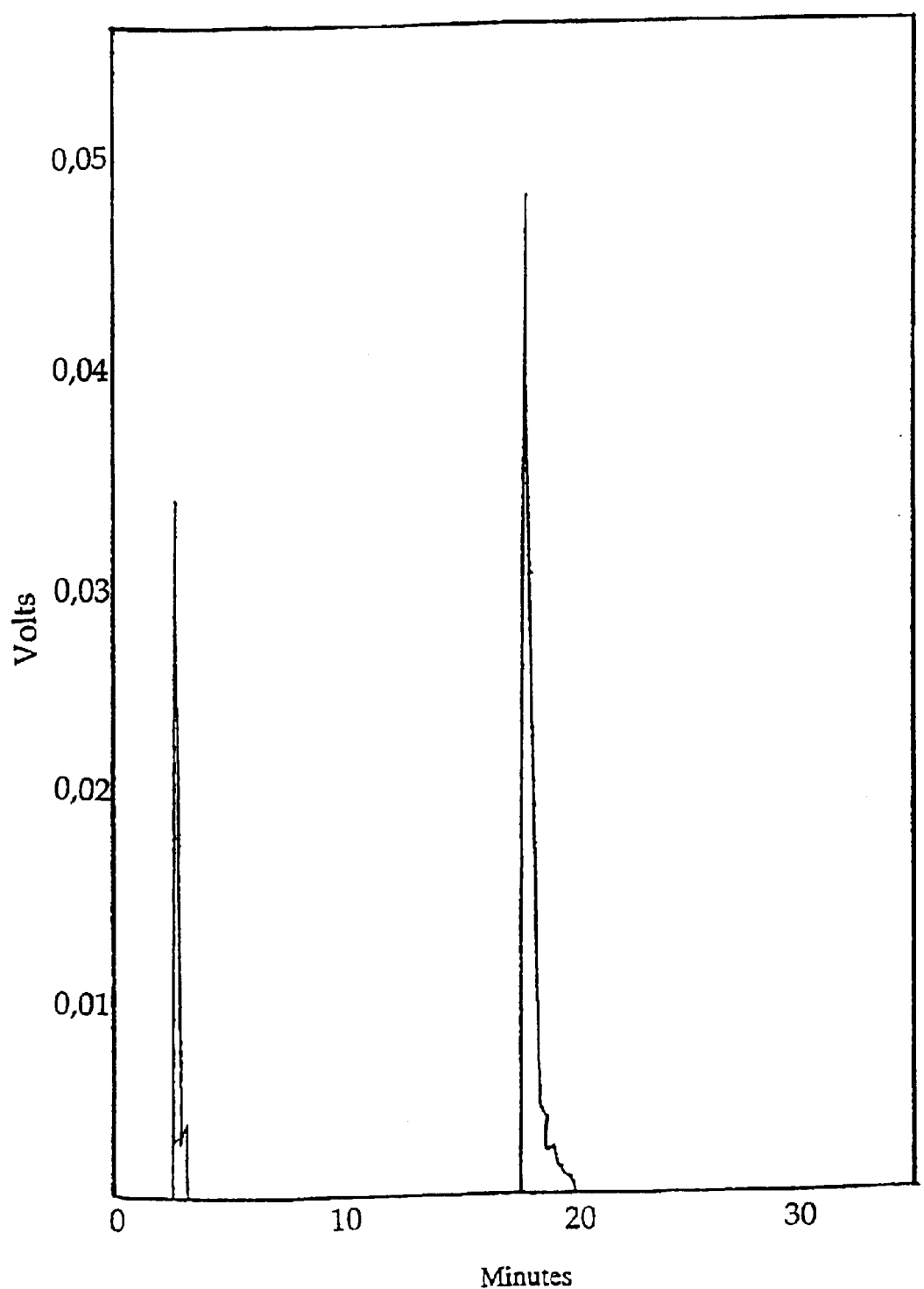
FIG. 2 is the HPLC elution of native insulin.
Figure 3:
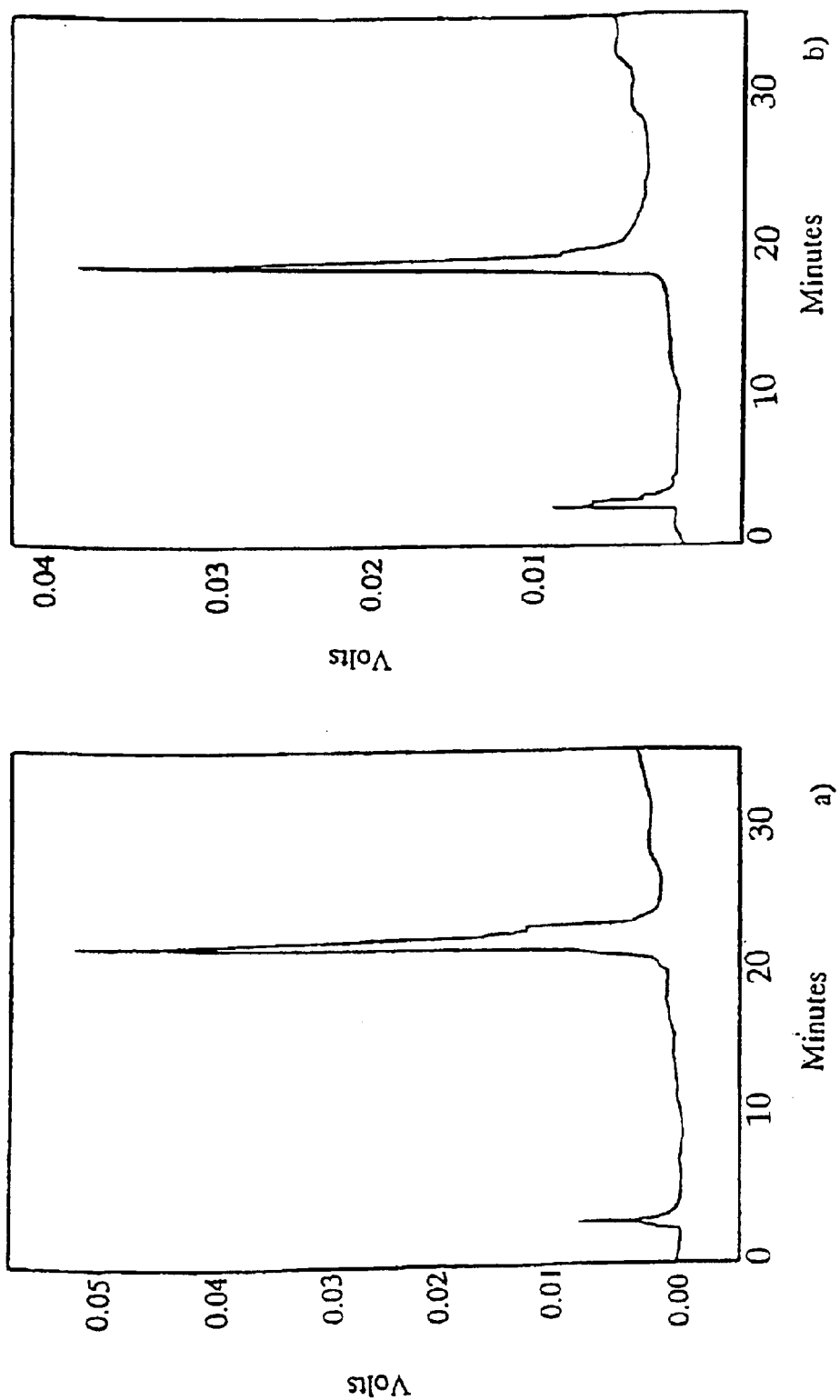
FIG. 3 a) is the HPLC elution of MPEG-Met-Nle-insulin; b) being the HPLC elution of Nle-insulin obtained from CNBr cleavage of MPEG-Met-Nle-insulin.
Figure 4:
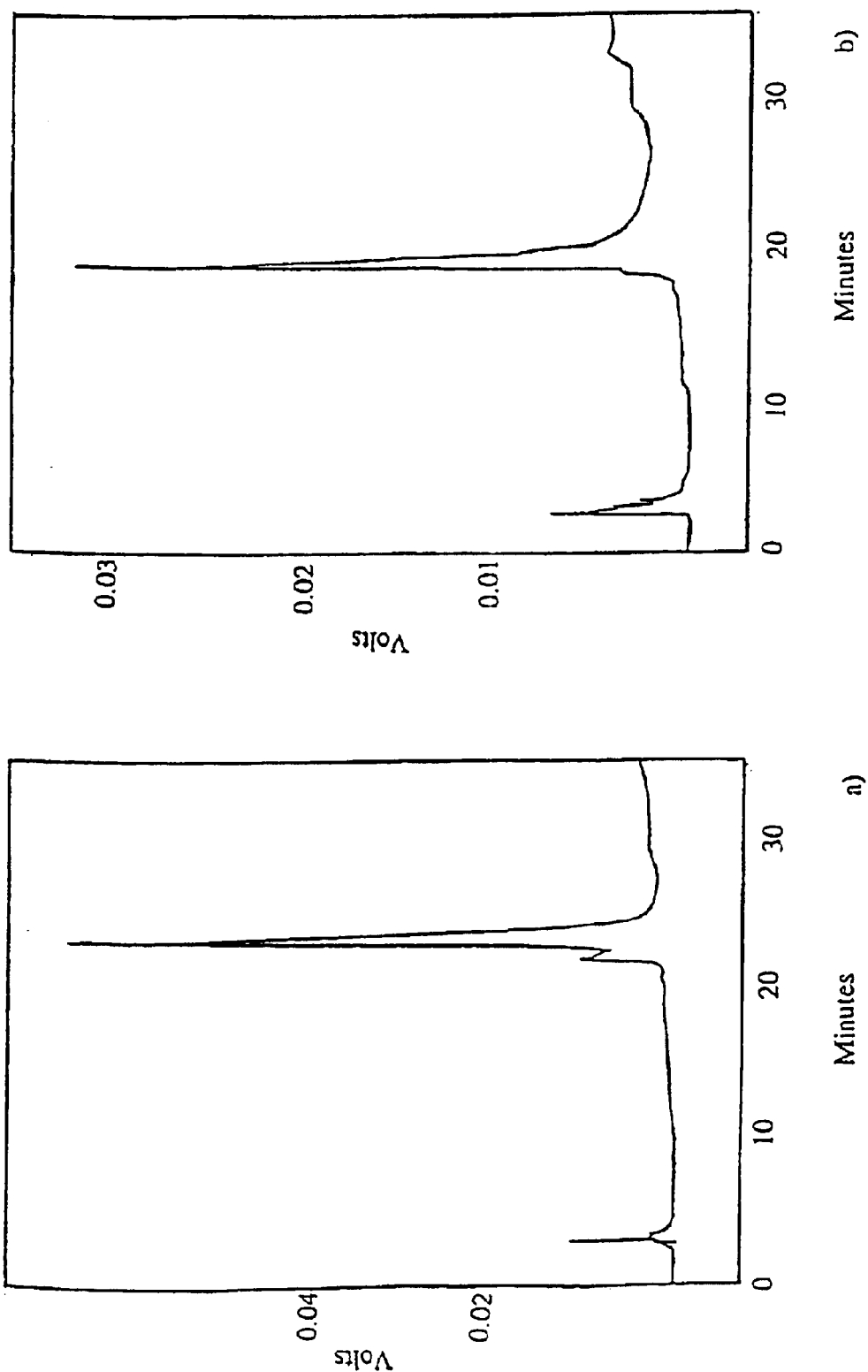
FIG. 4 a) is the HPLC elution of (MPEG-Met-Nle)$_2$-insulin; b) being the HPLC elution of (Nle)$_2$-insulin obtained from CNBr cleavage of (MPEG-Met-Nle)$_2$-insulin.
Figure 5:
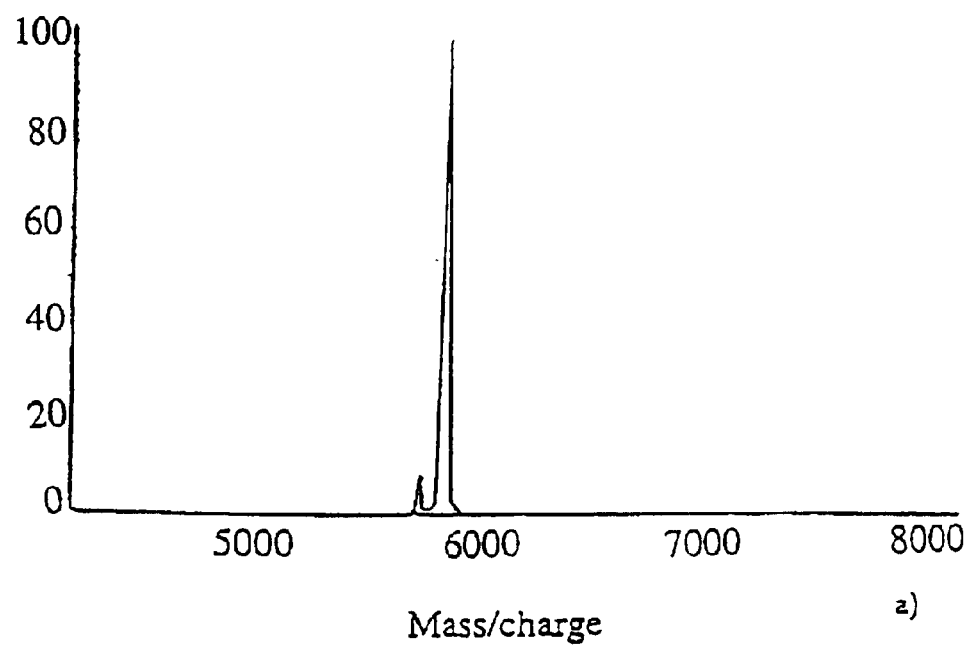
FIG. 5 a) is the Maldi mass spectrum of Nle-insulin obtained from CNBr cleavage of MPEG-Met-Nle-insulin, b) being the Maldi mass spectrum of (Nle)$_2$-insulin obtained from CNBr cleavage of (MPEG-Met-Nle)$_2$-insulin.
Figure 5:
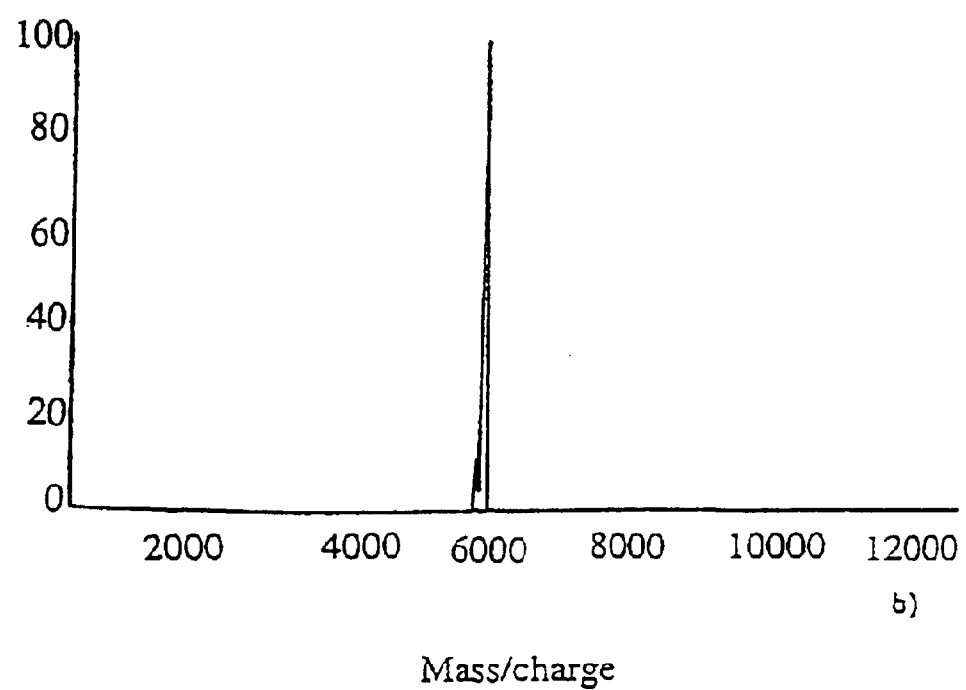

Evaluation of the Number of Polymer Chains Bound to Differently Modified Insulin Samples After Polymer Removal The products obtained as described in example 5 and 6 corresponding to insulin conjugates with one or two chains of MPEG-Met-Nle respectively, were treated with CNBr in aqueous 70% formic acid. The molar ratio between insulin content and CNBr was 1 to 200. After 24 hours stirring at room temperature, the mixture was poured into 10 volumes of water and lyophilised and the procedure was repeated twice. The obtained products were analysed by means of a Shimadzu analytical HPLC system, using a reverse-phase Vydac® 218TP54 column ($C_{18}$ bonded-phase, 0.46×25 cm i.d., 5 um particle diameter) and a linear gradient of aqueous 0.05% trifluoroacetic acid and 0.05% trifluoroacetic acid in acetonitrile. The elution pattern indicated a shift in the elution times from the 22.2 min. and the 23.2 min. for the PEG-insulin conjugates with one or two PEG chains respectively, to the 18.9 min. and the 19.2 min. for the products after CNBr cleavage. These values that are close to that of insulin alone (18.3 min.), demonstrated that the PEG moiety was removed (see FIG. 2, 3 e 4) The mass spectrometry analysis revealed a mass of one insulin molecule plus one Me residue when starting from the monoderivatized insulin (MPEG-Met-Nle-insulin) and plus two residues in the case of (MPEG-Met-Nle)$_2$-insulin. (see FIG. 5) The mass spectra patterns were by far more clear of those obtained in the analysis of the conjugates (examples 5 and 6) since the presence of the polymer, with its polydispersivity, makes the spectra and their interpretation more difficult and uncertain. Furthermore these values were confirmed by aminoacid analysis, finding that indicated one or two Nle residues present per insulin molecule in the samples.

All these data are in favour of the possibility to remove PEG from the molecule leaving Nle bound 10 and thus demonstrating the validity of the method.

EXAMPLE 9

Reduction and Carboxymethylation of Nle-insulin

500 µg (0.08 µmol) of Nle-insulin, obtained from MPEG-Met-Nle-insulin as described in example 8, were dissolved in 250 µl of TRIS-HCl buffer, pH 7.5, containing 2 mM EDTA and 6 M Gdn-HCl 3.8 ing of 1,4-dithio-L-threitol (DTT) were added and the mixture was left standing for 2 hours at 37° C. Finally 92 mg of iodoacetamide were added and the mixture was left for 1 hour at 37° C. The solution was lyophilised and the products fractionated by means of a Shimadzu semi-preparative HPLC system, using a reverse-phase Vydac® 218TP54 column ($C_{18}$ bonded-phase, 0.46× 25 cm Ld., 5 um particle diameter) with a linear gradient of aqueous 0.05% trifluoroacetic acid and 0.05% trifluoroacetic acid in acetonitrile. The eluted products monitored by absorption at 226 nm wavelength, revealed the presence of two main peaks, corresponding to chain α and β of insulin, that were separated and recovered. The aminoacid analysis after acid hydrolysis revealed Nle as additional aminoacid among those of chain β peak. The Edman degradation (according to *Protein Practical Chemistry*, pag. 371–373, 1986) released Phe and Nle at the first step, indicating that the α-amino group was free and consequently PEG was bound to $^{29}$Lys of chain β. Furthermore mass spectrometry analysis demonstrated that the increase of one Nle mass was present only in chain β.

EXAMPLE 10

Reduction and Carboxymethylation of Nle$_2$-insulin

600 μg (0.1 μmol) of Nle$_2$-insulin, obtained from MPEG-Met-Nle-insulin as described in example 8, were dissolved in 200 μl of TRIS-HCl buffer, pH 7.5, containing 2 mM EDTA and 6 M Gdn-HCl 7.6 mg of 1,4-dithio-L-threitol (DTT) were added in the mixture and left for 3 hours at 37° C. Finally 18.5 mg of iodoacetamide were added and left for 1 hour at 37° C. The solution was lyophilised and the products obtained were isolated and analysed as reported in example 9 for the Nle-insulin. By aminoacid analysis after acid hydrolysis, Nle aminoacid was found present in both chains α and β. Furthermore by mass spectrometry an increase in weight corresponding to one Nle residue was found in both chains. The data indicated that the PEGilation, in the conditions of example 6, took place at both chains.

EXAMPLE 11

Synthesis of MPEG-Met-Nle-lysozime 42.2 mg (7.8 μmol) of MPEG-Met-Nle-OSu were added, in small portions and under stirring, to 3.75 mg (0.26 μmol) of lysozime from egg white dissolved in 1 ml of 0.2 M borate buffer, pH 8.5. The molar ratio of lysozime amino groups:MPEG was 1:5. After 30 min. stirring at room temperature, the conjugate was purified by means of a semi-preparative FPLC system, using a gel-filtration Superose 12™ column (1.5×25 cm) eluted with 0.01 M phosphate buffer and 0.15 M NaCl, pH 7.2. The fractions were analysed for lysozime elution by absorption at 280 nm and iodine assay for PEG evaluation. The fractions containing the modified lysozime were collected and concentrated to small volume by ultrafiltration with an Amicon system using a YM3 membrane (cut off 3000). The concentrated solution was diluted with water and ultrafiltered. This procedure was repeated to remove the salts, and the product was finally lyophilised. By colorimetric amino group assay a degree of modification of 87% was calculated. A similar value was obtained on the basis of Nle content by aminoacid analysis after acid hydrolysis. A quantitative evaluation of the degree of modification by mass spectrometry was not reliable.

EXAMPLE 12

Figure 6:
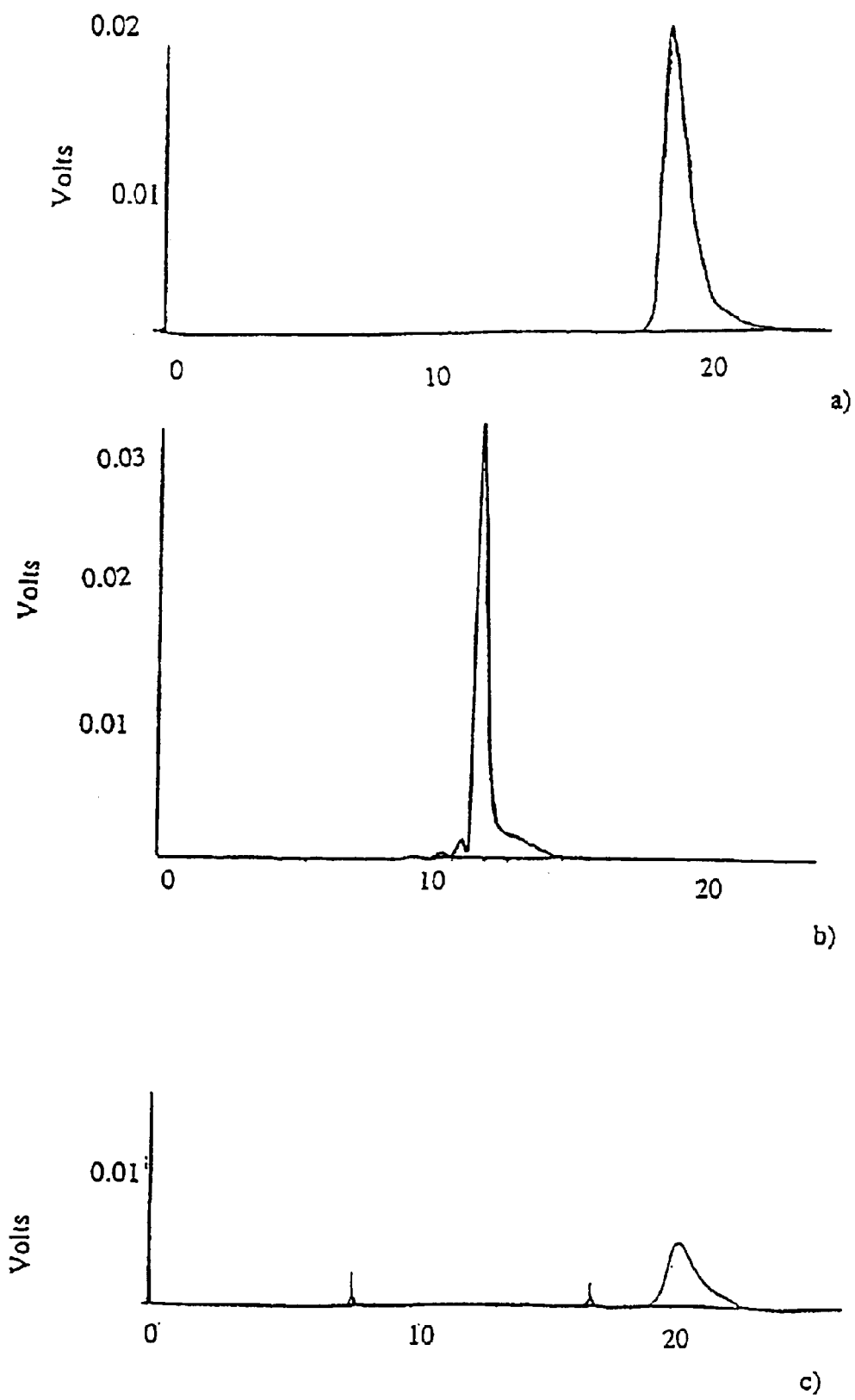
FIG. 6 is the chromatographic profile of a) native lysozime, b) being MPEG-Met-Nle-conjugate lysozime, c) being Nle-lysozime obtained from CNBr cleavage of MPEG-Met-Nle-conjugate lysozime.

Release of MPEG with CNBr to Obtain Nle-lysozime 0.04 μmol of the modified lysozime obtained as reported in example 11 were treated with 600 equivalents of CNBr in aqueous 70% formic acid, and left stirring for 24 hours at room temperature. The mixture was then poured into 50 ml of water and lyophilised (the procedure was repeated twice). The products obtained were analysed by gel filtration on a FPLC system, using the same column and elution conditions used for the polymer modified lysozime as reported in example 11, in order to compare the chromatographic profiles. It was found that the elution of lysozime peak, which appeared earlier upon polymer conjugation, shifted to approximately the original lysozime elution volume upon CNBr treatment. Correspondingly the amino groups tritrable by TNBS, which were reduced to approximately 10% upon lysozime modification with the polymer, returned to the values of unmodified lysozime after treatment with CNBr (see FIG. 6). The mass spectra patterns also were very clear and easy to interpretate as the weight of lysozime increased of 6 Nle residues. The aminoacid analysis revealed also a Nle amount close to that evaluated by TNBS assay and mass spectrometry. All of these data are in favour of the PEG conjugation to protein followed by its removal upon CNBr treatment but leaving Nle as reporter amino acid bound to the protein.

EXAMPLE 13

Interferon α-2b, mg 15, dissolved in 4 ml of borate buffer 0.1 M pH 7.8, was reacted with 100 mg of PEG-Met-Nle-Osu (10000 Da linear PEG or 10000 Da branched PEG). After 2 hours standing at room temperature the solution was brought to pH 6, concentrated by ultrafiltration and applied to the gel filtration column Superdex 200. Two peaks were obtained of differently modified interferon in addition to minor amount of unmodified protein. The PEG modified protein peaks maintained at large extent biological antiviral activity. The proteins were recovered by lyophylization and treated by BrCN as in example 12. In any case the release of PEG from the conjugated protein increase the elution volume, and the new volume corresponded to that of the unconjugated form, demonstrating the release of PEG form the conjugates as in example 12.

EXAMPLE 14

Interferon α-2b, was modified according to the procedure reported in example 13 but with PEG-Met-Nle-Osu of linear or branched of 20000 Da. In this experiment PEG 20000 Da with Met-β-Ala as peptide arm was used also.

In any case biologically active products were obtained. Furthermore, the treatment with BrCN released protein devoid of PEG but with Nle or β-Ala as reporter groups bound to the proteins.

EXAMPLE 15

Following the procedure of example 13 and 14, G-CSF was conjugated with PEG-Met-Nle-Osu of 10000 Da in the linear or branched form and of 20000 Da in the linear or branched form. PEG-Met-β-Ala was also used in the conjugation.

Biologically active protein was obtained in any case and PEG could be removed by BrCN treatment leaving Nle or β-Ala as reporter amino acid bound to the protein.

EXAMPLE 16

Following example 15, the glycoprotein erithropoietin was modified with PEG-Met-Nle or PEG-Met-β-Ala. Also in this case the conjugation yielded active protein and the release of PEG by BrCN treatment was achieved.

EXAMPLE 17

According to a similar procedure as the one described in Example 1, MPEG-Gln-Gly-OH has been prepared starting from MPEG-OH 5000and H-Gln-Gly-OH and then transformed into its succinimide activated ester MPEG-Gln-Gly-OSu.

EXAMPLE 18

According to a similar procedure as the one described in Example 5, the biological active conjugate MPEG-Gln-Gly-insulin has been obtained using the activated ester of Example 17. This conjugate demonstrated biological activities and was able to be selectively cleaved at the Gln-Gly bond applying a classical hydrazine treatment.

EXAMPLE 19

According to a similar procedure as the one described in Example 1, MPEG-Asp-Pro-OH has been prepared starting from MPEG-OH 5000 and H-Asp-Pro-OH and the transformed into its succinimide activated ester MPEG-Asp-Pro-OSu.

EXAMPLE 20

According to a similar procedure as the one described in Example 5, the biological active conjugate MPEG-Asp-Pro-insulin has been obtained using the activated ester of Example 19. This conjugate demonstrated is biological activities and was able to be selectively cleaved at the Asp-Pro bond by applying a classical mild aid treatment.

Abbreviations

As an aid to understanding the present invention, the following list of abbreviations used herein and easily comprehensive to a man of ordinary skill in the art is provided.
Asp Aspartic acid
Boc N-tert-Butoxycarbonyl
CMC 1-Cyclohexyl-3-(2-morpholinoethyl)carbodiimide metho-p-toluenesulfonate
DMSO Dimethyl sulfoxide
DTT 1,4-Dithio-L-threitol
EDTA Ethylenediaminetetraacetic acid
FPLC Fast protein liquid chromatography
Gdn-HCl Guanidine hydrochloride
HOBt 1-Hydroxybenzotriazole
HPLC High performance liquid chromatography
Leu Leucine
Lys Lysine
Met Methionine
MPEG or mPEG Poly(ethyleneglycol)methyl ether
Nle Norleucine
NMR Nuclear magnetic resonance
Nps 2-Nitrophenylsulfenyl
OMe Methoxy
OSu Succinimindyloxy
OtBu tert-Butoxy
PAcM Poly acryloylmorpholine
QAE Quaternary aminoethyl
Ser Serine
tBu tert-Butyl
TEA Triethylamine
Thr Threonine
TNBS 2,4,6-Trinitrobenzensulfonic acid
TRIS-HCl Tris(hydroxymethyl)aminomethane hydrochloride
Tyr Tyrosine
Val Valine

What is claimed is:

1. A biologically active conjugate derivative having the following general formula (I)

FE-L-M    (I)

where:
M represents the corresponding radical of a biologically active molecule selected from the group consisting of proteins, peptides, and polypeptides;
FE represents a functionalizing entity selected from the group consisting of PEG, PVP, PacM, dextran, hormones, antibodies, and antibody fragments; and
L represents a linking arm comprising a dipeptide selected from the group consisting of Met-Nle, Met-βAla, Gln-Gly, and Asp-Pro,
which is capable of being cleaved by chemical treatment to leave Nle, βAla, Gly or Pro, respectively, as a reporter group linked to M.

2. The biologically active conjugate derivative according to claim 1 characterised in that said functionalizing entity FE is a polymer with a molecular weight in the range of 2 Kd to 50 Kd.

3. The biologically active conjugate derivative according to claim 2 characterised in that said polymer is PEG.

4. The biologically active conjugate derivative according to claim 2 characterised in that said functionalizing entity FE is a linear polymer.

5. The biologically active conjugate derivative according to claim 2 characterised in that said functionalizing entity FE is a branched polymer.

6. The biologically active conjugate derivative according to claim 1 characterised in that said biologically active molecule is a protein selected from the group consisting of insulin, lysozyme, interferon, erythropoietin, G-CSF, and GH.

7. A method for identifying linkage sites of conjugation on the biologically active drug conjugate derivative of claim 1, which method comprises:
(a) cleaving the linking arm L comprising a dipeptide selected from the group consisting of Met-Nle, Met-βAla, Gln-Gly, and Asp-Pro;
(b) removing the functionalizing entity FE; and
(c) detecting Nle, βAla, Gly or Pro, respectively, as a reporter group linked to the biologically active molecule M to identify said linkage sites.

8. An intermediate compound, for the preparation of the biologically active conjugate of claim 1, having the following general formula (II)

FE-L    (II)

where:
FE represents a functionalizing entity selected from the group consisting of PEG, PVP, PacM, dextran, hormones, antibodies, and antibody fragments; and
L represents a linking arm comprising a dipeptide selected from the group consisting of Met-Nle, Met-βAla, Gln-Gly, and Asp-Pro.

9. The biologically active conjugate derivative according to claim 1 characterized in that said biologically active molecule is an interferon.

10. The biologically active conjugate derivative according to claim 9 characterized in that said biologically active molecule is interferon α-2b.

11. The biologically active conjugate derivative according to claim 1 characterized in that said biologically active molecule is selected from the group consisting of erythropoietin, G-CSF, and GH.

12. The biologically active conjugate derivative according to claim 1 characterized in that said linking arm is Met-Nle.

13. The biologically active conjugate derivative according to claim 1 characterized in that said linking arm is Met-βAla.

14. A biologically active conjugate derivative FE-L-M, wherein M represents the corresponding radical of a biologically active molecule which is an interferon, FE represents a functionalizing entity which is PEG, and L represents a linking arm comprising a dipeptide selected from the group consisting of Met-Nle, Met-βAla, Gln-Gly, and Asp-Pro.

15. An intermediate compound FE-L for the preparation of a biologically active conjugate, wherein FE represents a functionalizing entity which is PEG and L represents a linking arm comprising a dipeptide selected from the group consisting of Met-Nle, Met-βAla, Gln-Gly, and Asp-Pro.

* * * * *